(12) United States Patent
Tereschouk (10) Patent No.: US 6,358,214 B1
(45) Date of Patent: Mar. 19, 2002

(54) ECG SCANNER

(76) Inventor: Misha Tereschouk, P.O. Box 223, St. Petersburg (RU), 195279

( * ) Notice: Subject to any disclaimer, the term of this patent is extended or adjusted under 35 U.S.C. 154(b) by 0 days.

(21) Appl. No.: 09/375,240

(22) Filed: Aug. 17, 1999

Related U.S. Application Data (60) Provisional application No. 60/097,110, filed on Aug. 19, 1998.

(51) Int. Cl.$^7$ .............................................. A61B 5/0402
(52) U.S. Cl. ...................................................... 600/508
(58) Field of Search ................................. 600/509, 508, 600/512

(56) References Cited

U.S. PATENT DOCUMENTS 4,697,597 A * 10/1987 Sanz et al. ................... 600/512
5,458,116 A * 10/1995 Egler .......................... 600/512

* cited by examiner

Primary Examiner—George R. Evanisko (57) ABSTRACT

Electrocardiographic (ECG) scanner is a system for electrocardiological diagnostics by combining original ECG leads having known spatial positions into synthesized ECG leads having arbitrary spatial positions, analyzing electric signals of synthesized ECG leads, and producing scalar tracings (synthesized ECGs) in them. An ECG scanner automatically scans the three-dimensional space formed of a boundless number of synthesized ECG leads to detect the one which is collinear with a pathology and where earlier invisible or poorly discernible pathological ECG signs become noticeable or more manifesting and reaching diagnostic thresholds. An ECG scanner reveals diagnostically valuable information that is ordinarily lost in conventional electrocardiography and vectorcardiography. An automated ECG scanner includes: a device for systematically combining original ECG leads; a device for controlling parameters of combining ECG leads; a device for adjusting for a particular patient parameters of combining ECG leads; a device for analyzing electric signals of synthesized ECG leads; and a device for visualizing electric signals and positions of synthesized ECG leads. Supplementary devices are disclosed. A cardiac imaging system for matching heart structures of a patient with ECG signals originating therefrom is disclosed. A three-dimensional manipulator for manually ECG scanning is depicted.

14 Claims, 8 Drawing Sheets

| Sampling | Voltage (mV) in leads: | | | |
|---|---|---|---|---|
| time | V5 | S1 | S2 | S3 |
| 1 | -0.08 | -0.08 | -0.15 | -0.19 |
| 2 | -0.04 | -0.03 | 0 | -0.11 |
| 3 | -0.02 | 0 | 0.05 | -0.07 |
| 4 | -0.01 | 0 | 0.08 | -0.04 |
| 5 | 0 | 0.01 | 0.11 | -0.02 |
| 6 | 0 | 0.02 | 0.12 | -0.01 |
| 7 | 0 | 0.02 | 0.14 | 0 |
| 8 | -0.01 | 0.02 | 0.15 | 0 |
| 9 | -0.01 | 0.02 | 0.15 | 0 |
| 10 | -0.02 | 0.02 | 0.15 | 0 |
| 11 | -0.02 | 0.01 | 0.15 | 0 |
| 12 | -0.03 | 0 | 0.14 | 0 |
| 13 | -0.03 | 0 | 0.13 | 0 |
| 14 | -0.03 | 0 | 0.12 | 0 |
| 15 | -0.03 | 0 | 0.10 | 0 |
| 16 | -0.02 | 0 | 0.08 | 0 |
| 17 | -0.02 | 0 | 0.07 | 0 |
| 18 | 0 | 0 | 0.04 | 0 |
| 19 | 0 | 0 | 0.03 | -0.01 |
| 20 | 0 | 0.01 | 0 | -0.02 |

FIG. 8B

Scanning pattern: meridian-by-meridian.
Scanning step: 10°.
Scanning sector: meridian passing through V5.

Correlation coefficients

| Leads | Anterior wall | Posterior wall |
|---|---|---|
| X | 0,24 | 0,25 |
| Y | -0,24 | 0,74 |
| Z | -0,29 | 0,71 |
| S1 | -0,02 | 0,53 |
| S2 | 0,22 | 0,26 |
| S3 | 0,23 | -0,10 |
| S4 | 0,70 | -0,78 |
| S5 | -0,57 | 0,90 |

ECG SCANNER

This application claims benefits to Provisional Application No. 60/097,110 filed Aug. 19, 1998.

BACKGROUND OF THE INVENTION

1. Field of the Invention

The invention relates to electrocardiology, and more particularly to electrocardiographic (ECG) scanning.

2. Description of the Prior Art

The term "ECG lead" is used here to denote a vector at the ends of which a potential difference reflecting electric signals of the heart is sensed. An electrocardiogram (an ECG) is a tracing recorded in an ECG lead. The terms "synthesized lead" and "scanning lead" are used here interchangeably.

It is known that the collinearity of electrophysiologic activity of the heart with the direction of an ECG lead results in a most manifesting ECG pattern. It is an established practice to utilize fixed leads (such as 12 standard ECG, vectorcardiographic (VCG), body surface potential mapping (BSPM), or other lead sets) for ECG diagnosis. However, the collinearity cannot be always achieved with fixed leads, even with numerous BSPM leads. Pathological signs that are non-collinear with directions of the conventional leads do not always reach diagnostic thresholds and may be missed.

Positions of electrodes of the conventional ECG leads reflect historic preferences, convenience of electrodes placement, and proximity to the heart (and hence higher voltages) rather than the necessity to representatively demonstrate cardiac sources of electric potentials. Indeed, the unipolar chest leads are located almost in the same plane within one third of the circumference, scalar VCG presents electric signals of the heart as being projected on just three orthogonal leads, and BSPM does not show potential distribution at the top and bottom of the torso.

In the conventional electrocardiography propagation of electric signals of the heart to sensing electrodes is affected by extracardiac factors of different magnitude, which results in distorted propagation ways and variable impedance making voltages in different leads difficult to compare and analyze and requiring application of different voltage norms for the same parameter in different leads (e.g., different normal values for R-amplitudes or ST-deviation in chest and limb leads that reflect the same regions of the myocardium).

The indicated problems of utilizing ECG leads collinear with pathological changes, increasing the spatial coverage of ECG leads, and getting tracings of comparable voltages have been partially solved by a manual ECG scanner disclosed in the Russian patent #2077865 to Tereschouk. It has been shown that ECG diagnosis could be more accurate if ECGs are recorded in all directions. The patent discloses a manual ECG scanner that includes electrodes on a patient for sensing electric signals of the heart, synthesizer of three orthogonal leads from original leads sensed on a patient, synthesizer of ECG leads having arbitrary positions from the orthogonal leads, and an electrocardiograph. The synthesizer of ECG leads includes three channels. Each of the channels includes preamplifier, potentiometer, and phase inverter enabling arbitrariness of contributions of the three orthogonal leads, and hence arbitrariness of the position of a synthesized ECG lead.

By comparison with BSPM, an ECG scanner does not need a hundred of channels (and associated electrodes, wires, amplifiers, etc.) while it generates an unlimited number of leads embracing the whole three-dimensional space (including the top and bottom of the torso to observe inferior and basal segments of the myocardium) and is easier to perform and interpret. As opposed to the standard 12-lead ECG, an ECG scanner generates omnidirectional ECG leads producing tracings that are easier to analyze as they have comparable voltages. As distinct from VCG, which remains unpopular mainly due the intricacy of its interpretation, ECG scanning demonstrates electric signals of the heart specific for each spatial position of a scanning lead and presents results in a traditional scalar form without requiring extra training for physicians.

The manual ECG scanner of the prior art is useful for validating the new diagnostic principle of scanning the three-dimensional space to identify ECG leads exhibiting diagnostically significant signs and training in electrocardiology. However using three potentiometers in ECG scanning is confusing, time-consuming, and inconvenient. Thus an object of the present invention is to provide with an easy-to-use manipulator for a manual ECG scanning.

Manually ECG scanning is insufficiently accurate and effective, and thus hardly appropriate for the contemporary healthcare environment. The goal of this invention is to create an automated comprehensive ECG scanning system that could become a clinical routine.

In manually scanning of the prior art ECG leads are synthesized at irregular spatial and temporal intervals while the electric activity of the heart is different at different locations and changes over time making results of the prior art ECG scanning inaccurate, incomplete, and irreproducible. For example, a sign of myocardial infarction might be missed in a non-systematic ECG scanning, inasmuch as none of the synthesized ECG leads is collinear with that sign. In fluctuating cardiac pathology (dysrhythmia, conduction disorders) or deep breathing the temporal dissociation in synthesizing a number of ECG leads results in tracings reflecting absolutely different states of the heart that are impossible to analyze for the purposes of ECG scanning.

Therefore an object of this invention is to create an instrument for automatically and systematically synthesizing an array of ECG leads composing the three-dimensional space in a predetermined order to prevent information loss. Another object of the invention is to develop a method for automatically and systematically analyzing signals in an orderly-synthesized array of ECG leads to detect pathology in a lead that is collinear with a pathological sign.

Furthermore, an object of this invention is to make the process of ECG scanning controllable by an investigator, including building a means for selecting scanning parameters, such as diagnostic criteria.

The prior art does not recognize that parameters of ECG scanning should be adjusted for patients' electrophysiological variability. Therefore an object of this invention is to improve accuracy and reproducibility of ECG scanning by creating an automated learning system for adjusting parameters of combining ECG leads for a particular patient.

Another object of this invention is to make information about the three-dimensional position of a synthesized ECG lead readily available to an investigator.

Finally, an object of the current invention is to build a cardiac imaging system that would match changes in a patient's cardiac morphology and electrophysiology.

SUMMARY OF THE INVENTION

Electrocardiographic (ECG) scanner is a system for electrocardiological diagnostics by combining original ECG leads having known spatial positions into synthesized ECG leads having arbitrary spatial positions, analyzing electric signals of synthesized ECG leads, and producing scalar tracings (synthesized ECGs) in them. This invention improves manually ECG scanning of the prior art, and discloses automated ECG scanning.

It has been found that manually ECG scanning could be conducted more conveniently and effectively utilizing a three-dimensional rotating ball-type manipulator. A manipulator has three orthogonal sensors to set shares of the three respective orthogonal leads in a synthesized ECG lead. Each position of the ball of a manipulator corresponds to a fixed combination of shares of orthogonal leads determining a unique spatial position of a synthesized ECG lead. The ball is graduated to show to the investigator the spatial position of a synthesized lead. In a preferred embodiment the manipulator is a three-dimensional trackball, and its housing has an opening at about the equator of the rotating ball to ease manual rotation of the ball around its vertical axis through that opening.

It has been discovered that ECG scanning could be executed automatically providing with more comprehensive, accurate, and readily analyzable results if an ECG scanner included a means for systematically combining original ECG leads with known spatial positions into an array of synthesized ECG leads with arbitrary spatial positions. A means for combining ECG leads includes a means for calculating in a predetermined order shares of original leads in synthesized leads; a means for acquiring and combining synchronous electric signals of original leads in accordance with the calculated shares; and a means for computing positions of synthesized leads.

Furthermore, it has been found that a means for controlling parameters of combining ECG leads was fundamental for managing automatically scanning by an investigator and producing reliable and accurate scanning results. A means for controlling parameters of combining regulates spatial (constants, functions, independent variables and a range of their variations as determined by scanning pattern, step, and sector) and temporal (scanning time, period, rate) parameters of combining ECG leads. A scanning pattern is the systematic sequence, in which ECG leads are consecutively synthesized. A scanning step is the distance between consecutively synthesized ECG leads. A scanning sector is a part of the three-dimensional space that is selected for ECG scanning. A scanning time is the moment of a cardiac cycle that is selected for synthesizing ECG leads. A scanning period is the time period that is selected for synthesizing ECG leads. A scanning rate is the frequency that is selected for synthesizing ECG leads during a scanning period.

In a preferred embodiment, an ECG scanner utilizes the eight active channels of the conventional 12-lead electrocardiography as original leads to systematically synthesize ECG leads having arbitrary positions. A pair of dihedral angles $\alpha$ and $\beta$ (independent variables) of the global coordinate system determines the position of a synthesized lead. The shares of the eight channels in a newly synthesized ECG lead are equal to the products of the respective (i) shares of the eight channels in the three orthogonal leads X, Y, Z and (ii) shares of the three orthogonal leads in a synthesized lead. Shares of the eight channels in the three orthogonal leads (constants) are published. Shares of the three orthogonal leads in a newly synthesized lead are calculated by a means for calculating shares using the following formulae (functions):

share of $X = \cos\alpha \cos\beta$ share of $Y = \sin\alpha \cos\beta$ share of $Z = \cos\alpha \sin\beta$.

An ECG scanner includes a means for automatically analyzing synchronous electric signals of ECG leads, which includes a means for measuring synchronous electric signals of ECG leads; a means for comparing measurements; and a means for selecting measurements that meet predetermined criteria (extremeness of measured values, normal range, accepted diagnostic criteria, etc.).

An ECG scanner includes a means for visualizing electric signals of synthesized ECG leads. A synthesized ECG lead where pathological signs are mostly manifesting can be selected for continuous ECG monitoring. ECG scanning can be conducted in a patient during a stress test.

In order to make ECG scanning more accurate and reproducible, an ECG scanner includes a means for adjusting for a particular patient shares of original leads in synthesized leads, which results in minimum dissimilarity between homologous original and synthesized leads. In a preferred embodiment, a means for adjusting automatically adjusts shares of the eight active channels of the standard 12-lead electrocardiography in the three orthogonal leads. Thus adjusted shares are subsequently used for ECG scanning in that patient.

Knowing the position of a synthesized ECG lead is paramount for ECG scanning. For that purpose, a means for computing positions of synthesized leads is disclosed. In a preferred embodiment, automated ECG scanning is accompanied by building a three-dimensional image of a scanning lead, which is easy to comprehend.

A cardiac imaging system for non-invasively visualizing electric processes in the heart by matching heart structures of a patient with electric signals originating therefrom is disclosed.

Information on ECG scanning can be recorded by an appropriate means onto a suitable carrier for an off-line analysis, data interchange, storage, documentation, and other purposes.

In a preferred embodiment, an ECG scanner automatically scans the three-dimensional space formed of a boundless number of synthesized ECG leads to detect the one which is collinear with a pathology and where earlier invisible or poorly discernible pathological ECG signs become noticeable or more manifesting and reaching diagnostic thresholds. An ECG scanner can operate in a background mode while a routine ECG is taken, and show itself only when a pathological sign is automatically detected. ECG scanning can substitute for or enhance the standard 12-lead ECG and VCG, and effectively supplement any cardiac investigation. ECG scanning is easy to use, does not require much extra training for physicians, and is relatively inexpensive.

DETAILED DESCRIPTION OF THE INVENTION

An ECG scanner is a cardiac diagnostic instrument for scanning the three-dimensional space formed by a plurality of ECG leads. Manually ECG scanning is ordinarily accomplished by combining three orthogonal leads into synthesized ECG leads that have arbitrary spatial positions. The prior art ECG scanner utilizes three potentiometers to set contributions of three orthogonal leads. Using a three-dimensional manipulator of this invention makes manually ECG scanning more convenient and effective.

Figure 1:
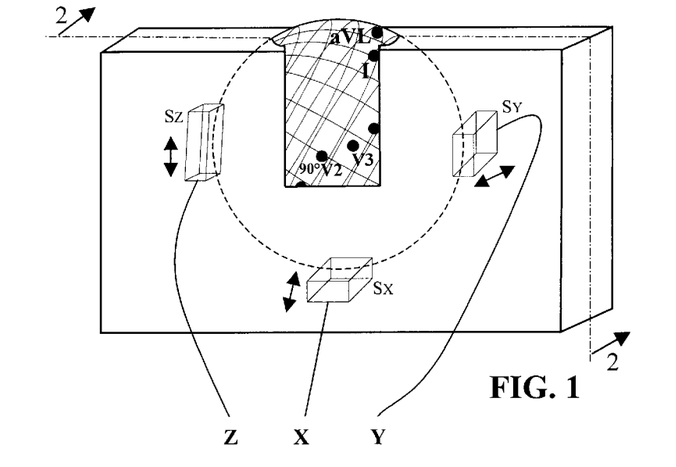
FIG. 1 is a perspective view of a three-dimensional trackball for ECG scanning.
Figure 2:
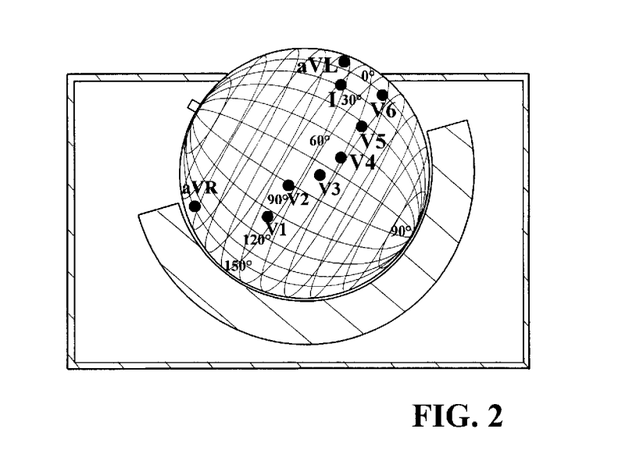
FIG. 2 is a cross-sectional view of a three-dimensional trackball for ECG scanning.
Figure 3:
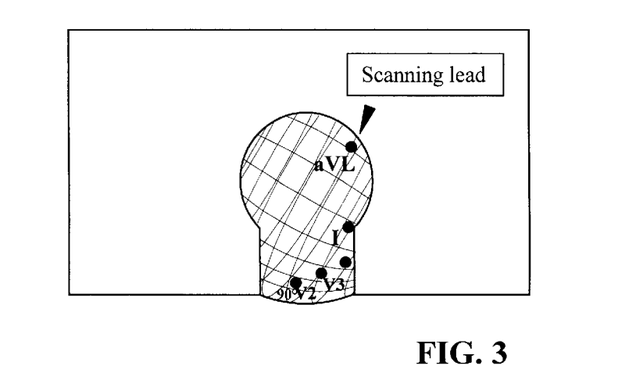
FIG. 3 is a top view of a three-dimensional trackball for ECG scanning.

A three-dimensional manipulator is of a rotating ball type (a trackball in a preferred embodiment or computer mouse). It has three orthogonal sensors for sensing rotation of the ball around orthogonal axes and setting shares of orthogonal leads in a synthesized ECG lead. FIGS. 1, 2 and 3 illustrate a three-dimensional trackball for a manual ECG scanning. The three orthogonal sensors $S_X$, $S_Y$, $S_Z$ are sensing rotation of the ball around its horizontal, vertical, and sagittal axes respectively (FIG. 1). Each orthogonal sensor sets the share of the respective orthogonal lead (X, Y or Z) in a synthesized lead. A synthesized lead represents a combination of shares of the three orthogonal leads.

Each position of the ball of a manipulator corresponds to a fixed combination of shares of the orthogonal leads determining a unique position (orientation) of a synthesized ECG lead. For that purpose, a ball may contain an eccentrically located magnet, the position of which is sensed by magnetic sensors. Similarly, a transparent ball may contain an eccentrically located nontransparent spot (inclusion) sensed by optical sensors.

Another solution is restricting rotation of the ball to 180° in any direction (the rationale is that in synthesizing ECG leads from orthogonal leads, synthesized leads of one hemisphere are inverse copies of synthesized leads of the other hemisphere). This can be realized by a suitable mechanical restraint. For example, a trackball may have projections that, when meet the edge of a hemispherical holder (or an annular support) of the ball, prevent its further rotation (FIG. 2).

The ball of a manipulator is graduated to show the position of a scanning lead in the three-dimensional space. In a preferred embodiment a ball is graduated in degrees, meridians, and parallels, like a globe, and also using landmarks (the end points of the three orthogonal and 12 standard ECG leads) (FIG. 2). Graduating the ball using global coordinates is justified, since the spherical surface of the ball can be viewed as being composed of the end points of all possible synthesized ECG leads that have a common origin at the center of the ball. The ball itself would represent the three-dimensional space formed by a plurality of those leads. It should be understood that a ball could be graduated using other navigational signs that help measuring the position of a synthesized lead in the three-dimensional space.

A three-dimensional manipulator with a graduated ball where each position of the ball corresponds to a fixed combination of shares of the orthogonal leads reduces the number of manual operations in ECG scanning. It also allows keeping the length of a synthesized lead constant resulting in synthesized ECGs of comparable amplitudes. In this embodiment ECG scanning is performed using a regular electrocardiograph or monitor for visualizing ECGs in synthesized leads without an additional means for visualizing directions of synthesized leads.

A ball of a three-dimensional trackball can be rotated around its vertical axis by grasping the ball with fingers (like a volleyball), and then turning it clockwise or counterclockwise. However it is less convenient and accurate than rolling the ball around its horizontal and sagittal axes. Therefore in a preferred embodiment of this invention a trackball has an opening at about the equator of the ball through which the protruding ball is rotated around its vertical axis by manually rolling (FIGS. 1, 3).

In a preferred embodiment, the housing of a three-dimensional manipulator is transparent (made of a transparent plastic) to see navigational marks of the ball and easily select the direction for a scanning lead. An index on the upper aspect of a trackball may point at a scanning lead (lead aVL on FIG. 3).

Figure 4:
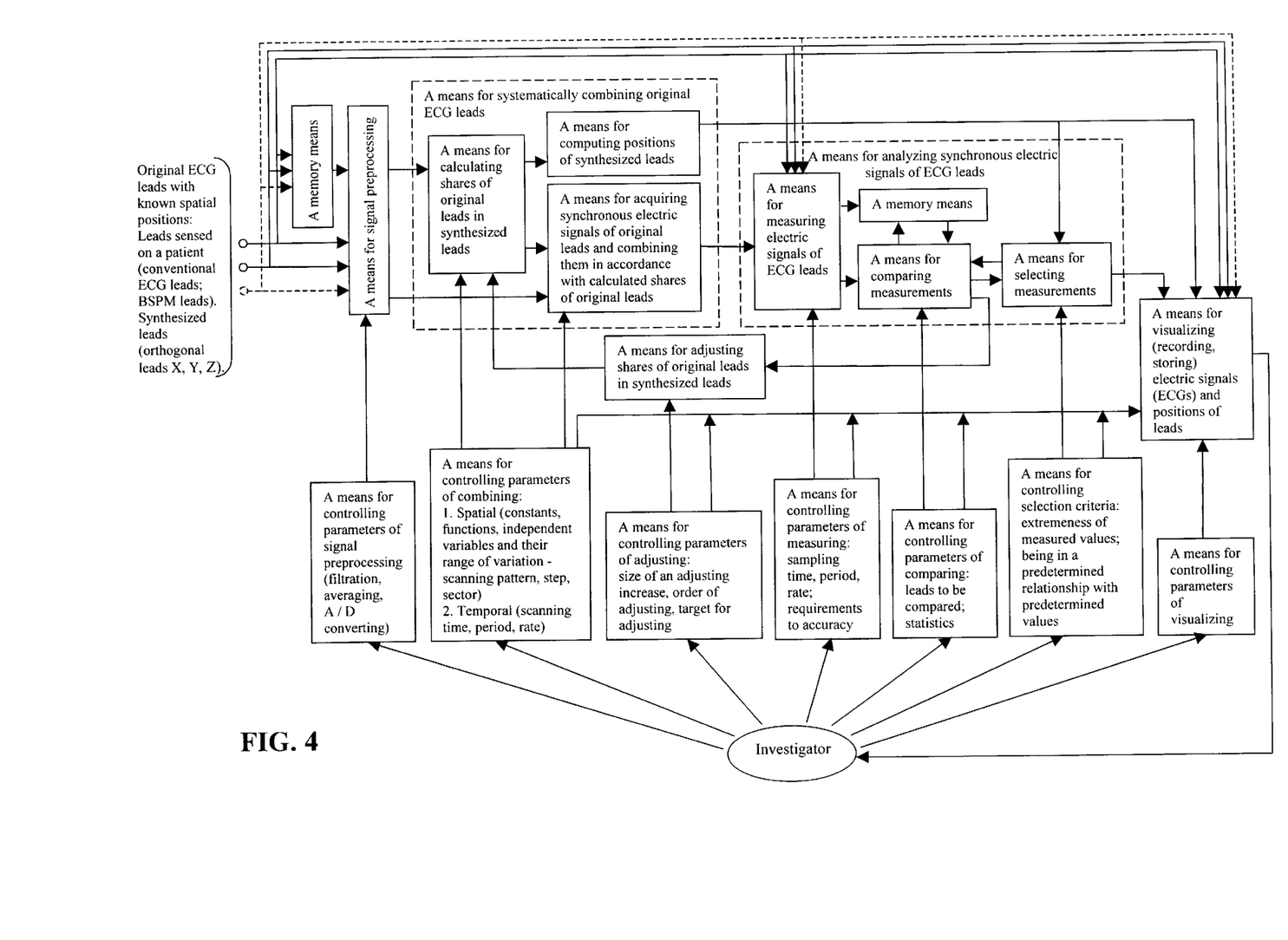
FIG. 4 is a block diagram representing operations of an automated ECG scanner.

An automated ECG scanner is a cardiac diagnostic instrument for automatically scanning the three-dimensional space formed by a plurality of synthesized ECG leads, which is accomplished by systematically combining original ECG leads that have known spatial positions into an array of synthesized ECG leads that have arbitrary spatial positions. FIG. 4 presents a block diagram of an automated ECG scanner.

An ECG scanner receives input data corresponding to electric signals of the heart from original ECG leads. Original ECG leads may be sensed on a patient or synthesized from leads sensed on a patient. Leads sensed on a patient may be the eight active channels (I, II, V1, V2, V3, V4, V5, V6) of the conventional 12-lead electrocardiography, leads used for BSPM, or another lead system where places of electrodes are significant for diagnosis. Leads synthesized from leads sensed on a patient may be the three orthogonal (vectorcardiographic) leads X, Y, and Z, which are synthesized using a resistor network (e.g., the Frank system utilized in the prior art ECG scanner) or electronically.

A means for signal preprocessing is used to make electric signals of original ECG leads adequate as input data for ECG scanning. Signal preprocessing may include filtration, averaging, and analog-to-digital converting of electric signals of original ECG leads. Parameters of signal preprocessing can be regulated by a corresponding means for controlling. For example, a 150–250 Hz bandwidth could be selected for ECG scanning of high-frequency components suggestive of coronary artery disease and twenty consecutive cardiac complexes could be elected for averaging.

It has been discovered that ECG scanning could be executed automatically providing with more comprehensive, accurate, and readily analyzable results if an ECG scanner included a means for systematically combining ECG leads with known spatial positions into an array of synthesized leads with arbitrary spatial positions. Systematically means utilizing the same function, such as formulae (1) below, for synthesizing all leads composing an array. A means for combining ECG leads includes a means for calculating shares of original leads in synthesized leads; a means for acquiring synchronous electric signals of the original leads and their combining in accordance with the calculated shares of the original leads in the synthesized leads; and a means for computing positions of the synthesized leads (FIG. 4).

A means for calculating shares of original ECG leads in synthesized ECG leads calculates shares, in which original leads have to be combined in order to synthesize a lead with a desirable position. Shares of original leads in synthesized leads are calculated in a predetermined order that reflects spatial (geometrical) interrelation between original and synthesized leads. A means for calculating shares calculates shares for each position of a scanning lead within a scanning sector (see definition of a scanning sector below). Any lead sensed on a patient can be utilized as an original lead in ECG scanning once its spatial position is known or its relation with an original lead that has already known spatial position is established.

Calculated shares of original leads in synthesized leads may be input data for a means for computing three-dimensional positions of synthesized ECG leads.

A means for acquiring and combining synchronous electric signals of original leads acquires synchronous (i.e. corresponding to the same single moment of a cardiac cycle) preprocessed electric signals of original ECG leads. It processes (amplifies and inverts) the acquired signals in accordance with shares (calculated by a means for calculating shares) of the original leads in each synthesized lead within a scanning sector and combines the processed signals. As a result, synchronous electric signals of original leads get modulated by shares of the respective original leads in synthesized leads and combined into synchronous electric signals of the synthesized leads. A plurality of synchronous electric signals of synthesized ECG leads forms an array that is automatically analyzed by an ECG scanner. Each array reflects electrical activity of the heart at a selected moment of a cardiac cycle as projected onto a plurality of synthesized leads. A time series of electric signals corresponding to a synthesized ECG lead represents a synthesized ECG in that lead.

A scanning system of the prior art is operating while sensing electric signals of the heart on a patient. An automated ECG scanner of this invention should generate and analyze big arrays of synchronous signals. To solve this problem, an ECG scanner includes a memory means for storing information corresponding to electric signals of original leads, and retrieves that information for synthesizing ECG leads. An automated ECG scanner can perform on-line (while being connected to the patient) or off-line (when it is disconnected from the patient), depending on the objectives and scope of ECG scanning. An off-line mode is useful when scanning takes more time than recording a standard ECG. A combination of on-line and off-line modes is possible. In a preferred embodiment of an off-line ECG scanning, signals in the three orthogonal leads obtained over a cardiac cycle are recorded onto a memory means and subsequently used for an off-line synthesis of ECG leads and analysis of electric signals in them.

The ability to produce arrays of synchronous signals on-line, one after another, would primarily depend on: processing capacity and random access memory (RAM) of an ECG scanner; scanning sector and step determining the number of synthesized leads in a scanning sector; and scanning period and rate determining the number of arrays (see definitions of the scanning sector, step, period, and rate below). For example, if a hemisphere is scanned at a 1°-step at 200 Hz-rate for 0.8 seconds, the number of synthesized ECG leads is $180^2 \times 2/\pi = 20{,}626$; the number of arrays is $200 \times 0.8 = 160$; and the number of electric signals to be combined into synthesized ECGs is $20{,}626 \times 160 = 3{,}300{,}160$.

An ECG lead of any spatial position can be synthesized with a varying degree of accuracy from at least two non-intersecting original ECG leads (represented by two solid parallel lines along the upper edge of the drawing on FIG. 4), such as leads used in the conventional 12-lead electrocardiography or BSPM. The lead system most widely used today is the standard 12-lead ECG system. The object of making ECG scanning more convenient is solved in a preferred embodiment by utilizing the eight active channels of the standard 12-lead ECG system as original ECG leads. In this embodiment an ECG scanner can perform automatically in a background mode, while a standard 12-lead ECG is taken, and inform the investigator if an ECG abnormality is detected.

The prior art teaches that ECG scanning includes the steps of, first, synthesizing the three orthogonal leads X, Y, and Z and then synthesizing arbitrary ECG leads from the three orthogonal leads. In automated ECG scanning of this invention, the step of synthesizing orthogonal leads can be omitted. In a preferred embodiment, the eight active channels of the conventional 12-lead electrocardiography sensed on a patient are combined into a new synthesized ECG lead in shares equal to the products of the respective (i) shares of the eight channels in three orthogonal leads and (ii) shares of the three orthogonal leads in the synthesized lead.

Published shares of the eight channels in the three orthogonal leads X, Y, Z are taken as constants in calculating shares of the eight channels in synthesized leads. TAB. 1 reproduces shares of the eight channels in the three orthogonal leads X, Y, Z from Kors J. A. et al. "Reconstruction of the Frank vectorcardiogram from standard electrocardiographic leads: diagnostic comparison of different methods", *Eur Heart J,* 1990, 11:1083–92; matrix C in the table on page 1084:

TABLE 1

| Leads | I | II | V1 | V2 | V3 | V4 | V5 | V6 |
|---|---|---|---|---|---|---|---|---|
| X | 0.38 | −0.07 | −0.13 | 0.05 | −0.01 | 0.14 | 0.06 | 0.54 |
| Y | −0.07 | 0.93 | 0.06 | −0.02 | −0.05 | 0.06 | −0.17 | 0.13 |
| Z | 0.11 | −0.23 | −0.43 | −0.06 | −0.14 | −0.20 | −0.11 | 0.31 |

It should be understood that instead of the eight channels of the standard 12-lead electrocardiography another set of original leads with electrode placements that are most significant for diagnosis (e.g., BSPM leads) can be selected for synthesizing orthogonal leads. Another alternative is to get orthogonal leads synthesized using the Frank leads and resistor network (as shown in the prior art) or similar vectorcardiographic lead systems.

Figure 5:
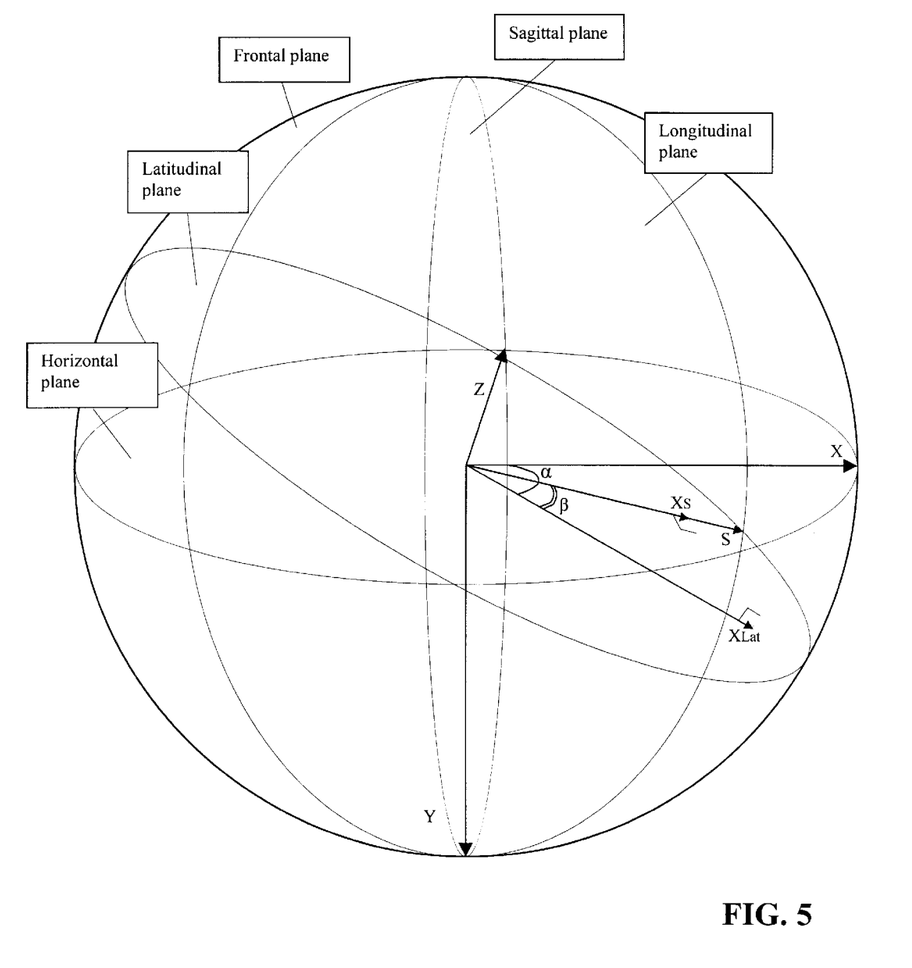
FIG. 5 shows the coordinate systems used in ECG scanning and illustrates the relationship between synthesized and orthogonal leads.

As discussed above, a plurality of all possible synthesized leads that have common starting point and equal lengths forms a globe. Therefore a global coordinate system utilizing dihedral angles (angle $\alpha$ for latitude and angle $\beta$ for longitude) may be convenient for determining the position of a synthesized ECG lead. FIG. 5 shows both the global and Cartesian coordinate systems in ECG scanning.

In a preferred embodiment angles $\alpha$ and $\beta$ are independent variables, and in ECG scanning their values orderly vary producing a number of systematically synthesized ECG leads. Alternatively, shares of orthogonal leads in synthesized leads can be selected as independent variables if Cartesian system is chosen.

FIG. 5 also illustrates the relationship between synthesized lead S and orthogonal lead X. Lead S goes right, backward and slightly down, its end point being at the intersection of the latitudinal and longitudinal (meridian) planes. The latitudinal plane forms angle $\alpha$ with the horizontal plane. The longitudinal plane forms angle $\beta$ with the frontal (prime meridian) plane. Lead X forms angle $\alpha$ with its normal projection onto the latitudinal plane ($X_{Lat}$). $X_{Lat}$ forms angle $\beta$ with its normal projection onto the synthesized lead S ($X_s$).

A function (a rule of correspondence between independent and dependent variables) for calculating shares for combining ECG leads can be determined by an appropriate formula, table, graph, etc. In a preferred embodiment, trigonometric formulae are used for calculating shares of the three orthogonal leads in synthesized leads. Shares of the orthogonal leads X, Y, and Z in a synthesized lead would be directly related to their normal projections onto it:

$$\text{share of } X = \cos\alpha \times \cos\beta$$

$$\text{share of } Y = \sin\alpha \times \cos\beta$$

$$\text{share of } Z = \cos\alpha \times \sin\beta \quad (1)$$

Voltage in a synthesized lead at any moment of time would be:

$$x \times \text{share of } X + y \times \text{share of } Y + z \times \text{share of } Z = x \times \cos\alpha \times \cos\beta + y \times \sin\alpha \times \cos\beta + z \times \cos\alpha \times \sin\beta, \quad (2)$$

where x, y, and z are synchronous measurements of voltage in the orthogonal leads X, Y, and Z.

As a result of systematically synthesizing ECG leads, the synthesized tracings have comparable voltages and become readily analyzable.

The following illustration might be helpful for understanding the described procedure. TAB. 2 provides with examples of utilizing formulae (1) for calculating shares of the orthogonal leads X, Y, and Z in six synthesized leads the spatial positions of which are determined by the respective pairs of angles $\alpha$ and $\beta$:

TABLE 2

| Synthesized leads: | 1 | 2 | 3 | 4 | 5 | 6 |
|---|---|---|---|---|---|---|
| $\alpha$ (degrees) | 0 | 0 | 0 | 45 | 30 | 30 |
| $\beta$ (degrees) | 0 | 45 | 90 | 45 | 30 | 60 |
| X | 1.00 | 0.71 | 0.00 | 0.50 | 0.75 | 0.43 |
| Y | 0.00 | 0.00 | 0.00 | 0.50 | 0.43 | 0.25 |
| Z | 0.00 | 0.71 | 1.00 | 0.50 | 0.43 | 0.75 |

In order to synthesize the exemplary six leads of TAB. 2 from the eight active channels of the standard 12-lead ECG, the shares of the eight channels in the synthesized leads are calculated as the products of the respective shares in TAB. 1 and 2:

TABLE 3

| Synthesized leads: | 1 | 2 | 3 | 4 | 5 | 6 |
|---|---|---|---|---|---|---|
| $\alpha$ (degrees) | 0 | 0 | 0 | 45 | 30 | 30 |
| $\beta$ (degrees) | 0 | 45 | 90 | 45 | 30 | 60 |
| I | 0.38 | 0.35 | 0.11 | 0.21 | 0.30 | 0.23 |
| II | −0.07 | −0.21 | −0.23 | 0.32 | 0.25 | 0.03 |
| V1 | −0.13 | −0.40 | −0.43 | −0.25 | −0.26 | −0.36 |

TABLE 3-continued

| Synthesized leads: | 1 | 2 | 3 | 4 | 5 | 6 |
|---|---|---|---|---|---|---|
| $\alpha$ (degrees) | 0 | 0 | 0 | 45 | 30 | 30 |
| $\beta$ (degrees) | 0 | 45 | 90 | 45 | 30 | 60 |
| V2 | 0.05 | −0.01 | −0.06 | −0.02 | 0.00 | −0.03 |
| V3 | −0.01 | −0.11 | −0.14 | −0.10 | −0.09 | −0.12 |
| V4 | 0.14 | −0.04 | −0.20 | 0.00 | 0.04 | −0.07 |
| V5 | 0.06 | −0.04 | −0.11 | −0.11 | −0.08 | −0.10 |
| V6 | 0.54 | 0.60 | 0.31 | 0.49 | 0.60 | 0.50 |

Then, similarly to the action described by formulae (2), a means for combining electric signals combines digitized synchronous (i.e. acquired at the same selected moment of a cardiac cycle) electric signals corresponding to the eight channels into electric signals corresponding to the six synthesized leads in accordance with the shares calculated for each of the six leads in the respective column of TAB. 3. As a result, an array of six combined electric signals is generated for each moment of a scanning period. A time series of combined electric signals of a synthesized lead obtained over a scanning period represents a synthesized ECG. The six synthesized ECGs are then examined by an investigator or analyzed by an ECG scanner automatically.

Though the transformation of orthogonal leads into leads of arbitrary directions is well comprehensible, it should be understood that ECG scanning could utilize other reliable transformations to synthesize other types of leads that have arbitrary spatial positions. For example, it would be obvious to synthesize ECG leads that do not have a common origin from BSPM leads.

It has been found that a means for controlling parameters of combining ECG leads was fundamental for managing the automated ECG scanning by an investigator, and producing reliable and accurate scanning results (FIG. 4). A means for controlling parameters of combining regulates spatial (constants, functions, independent variables and a range of their variations as determined by a scanning pattern, step, and sector) and temporal (a scanning time, period, and rate) parameters of combining original leads into synthesized leads.

Constants, functions, and independent variables for calculating shares of original leads in synthesized leads have been discussed above. The range of variations of independent variables (which in the preferred embodiment are dihedral angles $\alpha$ and $\beta$) is determined by scanning pattern, step, and sector.

A scanning pattern is a systematic sequence, in which ECG leads are consecutively synthesized. New ECG leads can be synthesized in a meridian-by-meridian (FIG. 6), parallel-by-parallel (FIG. 7), or any other non-repeating sequence (e.g., a sequence where the shares of orthogonal leads X, Y, Z consecutively and stepwise assume all possible values from 0 to 1 (maximum) producing all possible combinations). A scanning pattern determines scanning conditions. For example, in a meridian-by-meridian scanning, angle $\beta$ is kept constant within each meridian while angle $\alpha$ changes stepwise; in a parallel-by-parallel scanning, the share of lead Y is kept constant for each parallel while the shares of leads X and Z incrementally change.

A scanning step is the distance between consecutively synthesized ECG leads. Scanning steps may be different for different planes. In the example of meridian-by-meridian scanning (FIG. 6), the step between the consecutively synthesized leads lying in the same meridian is 10°, while the step between adjacent meridians is 15°. In the example of parallel-by-parallel scanning (FIG. 7), the step between the consecutively synthesized leads pointing at the same parallel is 10°, while the step between adjacent parallels is 15°. The smaller is the step, the greater is the number of leads synthesized for a given scanning sector. A reasonable scanning step is 1–5°.

A scanning sector is a part of the three-dimensional space that is selected for ECG scanning (synthesizing ECG leads). Since a plurality of all synthesized ECG leads having equal lengths and originating from the same point forms a globe, the spherical surface of which is formed by the end points of those leads, a scanning sector would be a sector of that globe (or sphere). Examples of a scanning sector may be: one meridian (FIGS. 6, 8) or parallel (FIG. 7); a 15°-sector around a particular conventional lead (e.g., around lead aVF or V1); an anterolateral aspect of the sphere where pathological signs have been recorded in a patient or could be expected based on the history or examination results; an area of the right chest leads in a patient with signs suspicious for anterior or right ventricular myocardial infarction; or a whole hemisphere.

Figure 6A:
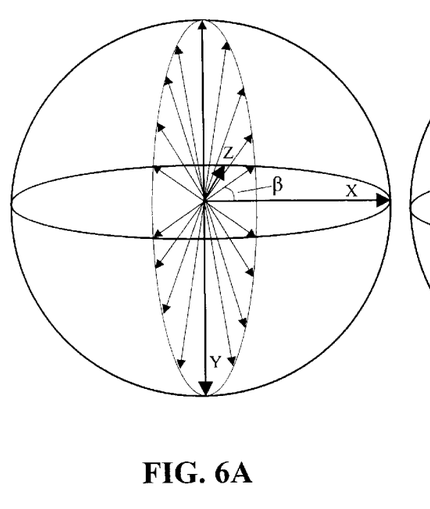
FIG. 6 illustrates meridian-by-meridian ECG scanning.
Figure 6B:
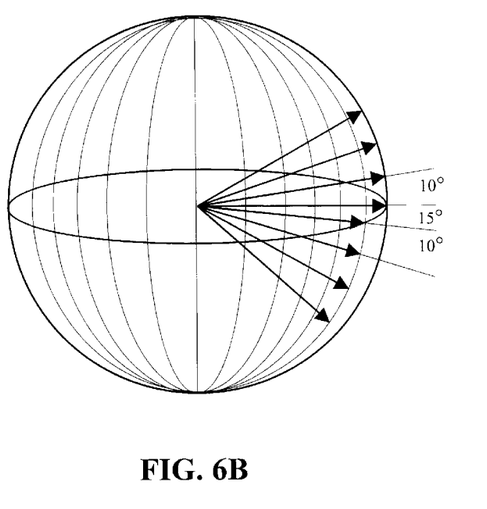
Figure 7A:
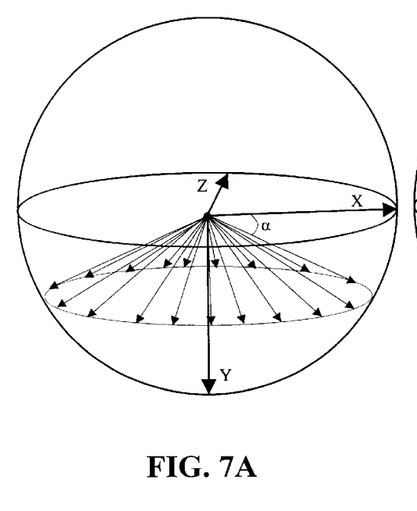
FIG. 7 illustrates parallel-by-parallel ECG scanning.
Figure 7B:
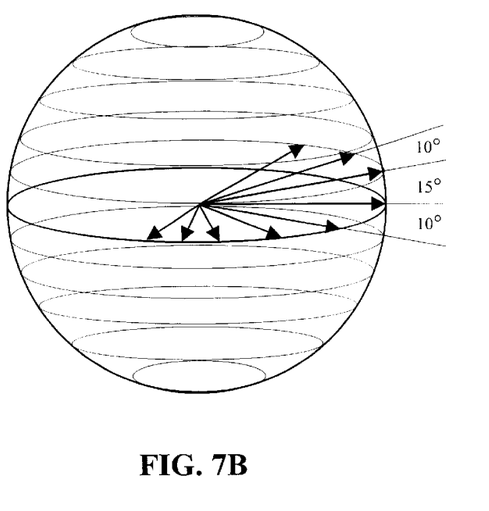

TAB. 4 shows shares of the eight channels of the standard 12-lead electrocardiography in the first six synthesized leads of the meridian sector depicted on the left drawing of FIG. 6. The shares are calculated based on the following parameters of combining:

| Constants: | data from TAB. 1 |
|---|---|
| Function: | formulae (1) |
| Range of variations of independent variables: | scanning pattern: meridian-by-meridian. scanning step: 10° within a meridian. scanning sector: just one meridian, $\beta = 70°$. |

TABLE 4

| Synthesized leads: | 1 | 2 | 3 | 4 | 5 | 6 |
|---|---|---|---|---|---|---|
| $\alpha$ (degrees) | 0 | 10 | 20 | 30 | 40 | 50 |
| $\beta$ (degrees) | 70 | 70 | 70 | 70 | 70 | 70 |
| I | 0.23 | 0.23 | 0.21 | 0.19 | 0.16 | 0.13 |
| II | −0.24 | −0.18 | −0.12 | −0.05 | 0.02 | 0.09 |
| V1 | −0.45 | −0.44 | −0.41 | −0.38 | −0.33 | −0.27 |
| V2 | −0.04 | −0.04 | −0.04 | −0.04 | −0.03 | −0.03 |
| V3 | −0.13 | −0.14 | −0.13 | −0.13 | −0.11 | −0.10 |
| V4 | −0.14 | −0.13 | −0.12 | −0.11 | −0.09 | −0.07 |
| V5 | −0.08 | −0.09 | −0.10 | −0.10 | −0.10 | −0.10 |
| V6 | 0.48 | 0.48 | 0.46 | 0.43 | 0.39 | 0.34 |

A scanning time is the moment of a cardiac cycle that is selected for synthesizing ECG leads that constitute a scanning sector. Alternatively, a scanning time may be defined as the moment of a cardiac cycle selected for generating an array of synchronous signals of synthesized leads if a means for calculating shares of original leads and a means for acquiring and combining synchronous signals of original leads (FIG. 4) do not perform simultaneously (e.g., when a means for calculating shares calculates shares of original leads for all synthesized leads within a scanning sector, and then a means for acquiring and combining signals utilizes thus calculated shares to combine electric signals of original leads at each moment of a cardiac cycle under examination, array after array). A scanning time may be a particular moment during a cardiac cycle when abnormal or atypical ECG signs have been recorded or are anticipated (e.g., a notch on S-wave or j-point).

A scanning period is the time period that is selected for synthesizing ECG leads that constitute a scanning sector. Alternatively, a scanning period may be defined as the time period during which arrays of synchronous signals of synthesized leads are generated if, as explained above, a means for calculating shares and a means for acquiring and combining signals do not perform simultaneously. A scanning period may be determined by its starting and end points (e.g., from the beginning of Q-wave to the beginning of T-wave), by its starting (or end) point and duration (e.g., within 0.05 sec before and after R-peaking), or as a part or whole of a cardiac cycle, or in any other suitable manner. A scanning period may include all beats sensed on a patient (or stored in a memory means) or just one averaged cardiac complex or its part. The scanning period on FIG. 8 lasts for 0.8 sec and includes one cardiac cycle.

A scanning rate is the frequency that is selected for synthesizing ECG leads that constitute a scanning sector during a scanning period. Alternatively, a scanning rate may be defined as the frequency of generating arrays of synchronous signals of synthesized leads during a scanning period if, as noted above, a means for calculating shares and a means for acquiring and combining signals do not perform simultaneously. A scanning rate may be selected rather than scanning times if ECG scanning is to be accomplished at multiple scanning times. A scanning rate is the inverse of the time between synthesizing consecutive arrays. For example, if ECG leads are synthesized every 0.005 sec, the scanning rate is 200 Hz (=1/0.005). A scanning rate has to be sufficiently high in order not to miss important diagnostic signs. However, the higher the scanning rate, the more leads (or the more arrays of synchronous signals) have to be synthesized for a given scanning period. To obtain a smooth synthesized ECG, a scanning rate should be higher than 200 Hz.

A means for analyzing synchronous electric signals of ECG leads includes a means for measuring electric signals of ECG leads, a means for comparing measurements, a means for selecting measurements, and a memory means (FIG. 4).

A means for measuring electric signals measures electric signals (voltage in a preferred embodiment) in ECG leads (both synthesized and original). For the purposes of ECG scanning, measuring synchronous (i.e. corresponding to the same moment of a cardiac cycle) electric signals is most important. A means for controlling parameters of measuring allows selecting the time, period, and rate for sampling synchronous electric signals that are going to be analyzed and requirements to accuracy of measurements. An example of the accuracy would be a 1%-error in measuring that is considered acceptable.

A means for comparing compares measurements of electric signals of different ECG leads (original, synthesized, stored in a memory means). A means for controlling parameters of comparing is used to select leads to be compared and applicable statistics (e.g., a significant difference between compared values).

A means for selecting selects measurements that meet predetermined selection criteria. Selection criteria are established by a correspondent means for controlling and may include extremeness (i.e. minimum or maximum) of measurements and being in a predetermined relationship (e.g., within a 15%-range) with predetermined values (normal values, accepted diagnostic criteria, values measured in the same patient previously, expected values, etc.). An automated ECG scanner systematically spans the three-dimensional space composed of ECG leads of all possible directions preventing information loss and accurately locates leads that are collinear with a pathology and where earlier invisible or poorly discernible pathological ECG signs reach diagnostic thresholds (selection criteria) and become visually noticeable or more manifesting.

Suppose an investigator orders to find ECGs demonstrating the biggest elevation of ST-segment in the left chest region. Scanning along the meridian passing through the conventional lead V5 with a scanning step of 10° results in synthesizing eighteen ECG leads the first three of which (S1, S2, and S3) are shown on FIG. 8. Voltage measurements at twenty sampling times are listed in the table. The ECG in lead V5 does not reveal any apparent pathology while a prolonged ST elevation above 0.1 mV in the synthesized lead S2 at the sampling times 5–14(bold values in the table) are diagnostically significant and would have been missed if the problem sector had not been scanned.

Figures 8A, 8B, 8C:
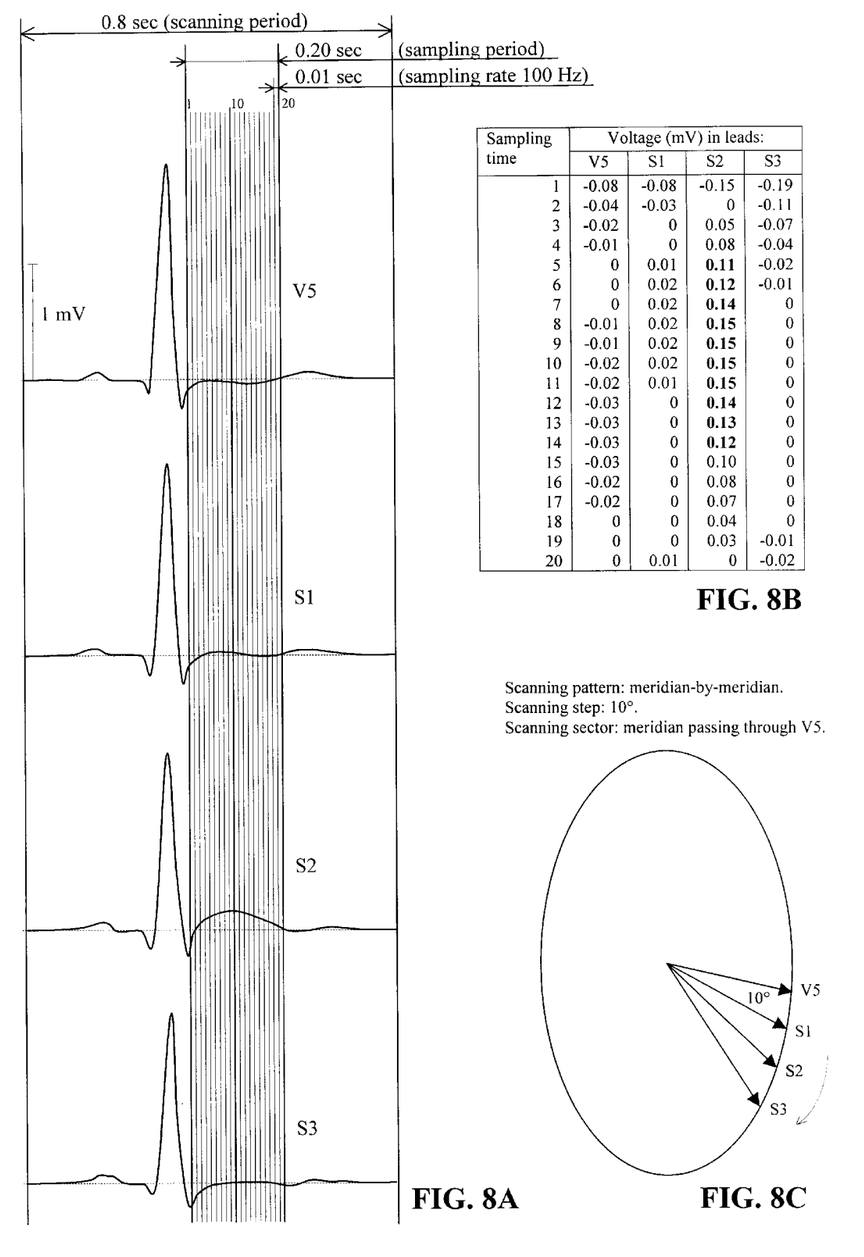
FIG. 8 demonstrates an array of synthesized ECGs and positions of the corresponding leads.

The period and rate of acquiring synchronous electric signals should exceed or equal the period and rate of their combining (sampling). For example, electric signals of original leads may be acquired over a scanning period of 0.8 sec at a scanning rate of 200 Hz, but only a portion of them corresponding to 0.2 sec of ST-segment is then combined (sampled) into synthesized tracings at a rate of 100 Hz (FIG. 8).

An analysis of synchronous electric signals in an array can be performed by an in pair comparison. For example, if an ECG scanner is programmed to find the highest R-peak, a means for comparing selects the higher value in a pair of measurements of R-wave amplitudes that are synchronously acquired in two consecutively synthesized ECG leads. The higher value is stored in a memory means (RAM). A value of a lesser significance is deleted. The stored value is then compared with another measurement acquired in the next synthesized lead, and so on. Ultimately, after comparing all synchronous signals within an array, a means for selecting makes the R-wave amplitude that is the highest in the array, synthesized ECG containing that R-wave, and position of the corresponding synthesized ECG lead available for visualizing by a means for visualizing (FIG. 4). The results of an automated ECG analysis can be also recorded onto a memory means.

It should be understood that various algorithms for analyzing arrays of synchronous electric signals can be used. To accelerate analysis of a big array, techniques ordinarily used in computerized analysis of big databases (e.g., a parallel processing) may be applied.

An automated ECG scanner can: measure voltage in a synthesized lead of an arbitrary direction and find a synthesized lead with the highest (or lowest) voltage at a particular moment of a cardiac cycle; accurately identify the starting and end points of ECG waves and measure their maximal duration and amplitude; determine a maximal deviation from the baseline; detect micropotentials; locate and quantify the maximum and spatial spread of pathological foci forming basis for topical ECG diagnosis; etc.

To illustrate, an ECG scanner can locate a lead that is collinear with ST-deviation and where the area-under-curve (AUC) over-ST-segment (total ischemic burden) is maximum. The selected lead could be used for subsequently monitoring the AUC. The spatial spread of ischemia (area and form of the spread; volume-under-surface which the integral of AUCs for all leads composing the three-dimensional space) could be also measured and monitored.

Another example is locating the biggest notch and quantifying it as the amplitude or largest AUC over a period that has equipotential starting and end points. An early bite on the descending portion of S-wave undetected in the conventional leads V1–3 and vectorcardiographic horizontal loop in a patient with anterior myocardial infarction could have been identified if ECG scanning had been performed in the vicinity of the conventional right chest leads. A wide Q-wave indicative of inferior myocardial infarction may not be apparent in the conventional leads II, III, aVF and vectorcardiographic frontal loop, but becomes noticeable in a tracing of a synthesized lead going down and slightly backward from the frontal plane.

Automatically detecting a lead producing the greatest acceleration (derivative of velocity) of the change of a potential difference might help identifying peaks and notches in conduction disorders, early repolarization, and other conditions.

A scanning lead producing signs suspicious for cardiac pathology can be selected for monitoring during a physical stress (exercise) test. Likewise, scanning the sector where pathological signs could be expected (e.g., a zone of healed myocardial infarction) under stress might reveal signs that go unnoticed in a regular examination.

An ECG scanner includes a means for visualizing electric signals in ECG leads (FIG. 4) that may be an electrocardiograph, ECG monitor, a computer monitor, etc. A lead producing a most manifesting ECG sign (e.g., the highest ST-elevation) can be selected for visualizing by a means for continuous ECG monitoring, ambulatory or in-hospital (in intensive care units, during cardiac interventions such as angioplasty, ablation of conduction pathways, etc.). A means for visualizing can simultaneously display electric signals (ECGs) and positions (image, direction, coordinates) of several original and synthesized leads.

In a preferred embodiment a means for visualizing displays ECGs and positions of the respective synthesized leads together with a multiplane VCG of the patient that could be rotated on the screen by the investigator seeking for most informative positions of the scanning lead (this is similar to finding the optimum position for M-mode in echocardiographic scanning).

Since spatial positions of synthesized ECG leads in the chest are known, it is possible to non-invasively visualize electric processes in the heart by matching heart structures of a patient with electric signals of synthesized ECGs.

Figure 9A:
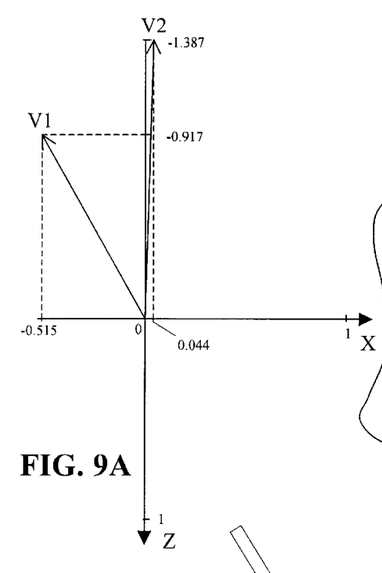
FIG. 9 illustrates ECG mapping at a cross-sectional view of the thorax.
Figure 9B:
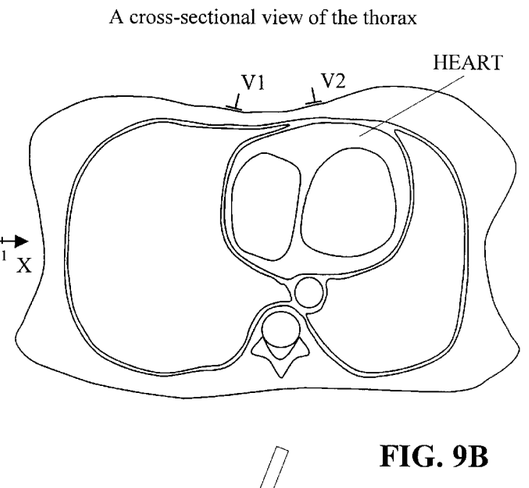
Figure 9C:
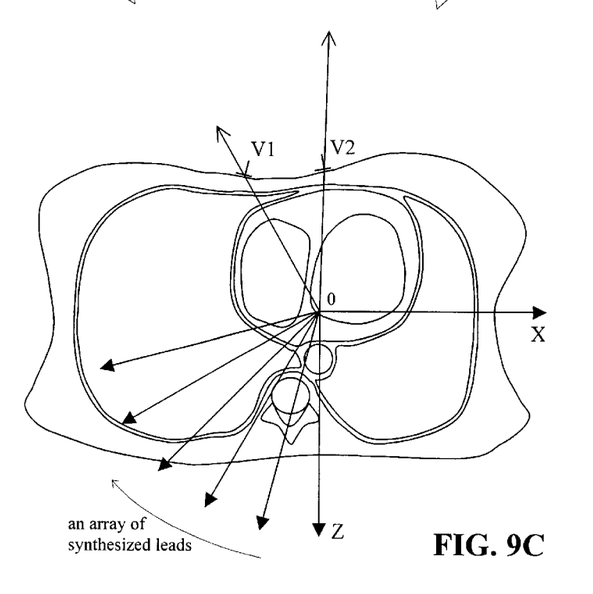

FIG. 9 shows a cross-sectional view of the thorax (as seen in computed tomography or magnetic resonance imaging) at the level of the chest electrodes V1 and V2. Synthesized leads V1 and V2 are generated from the orthogonal leads X, Y, and Z using published coefficients (Dower G. E. , Machado H. B. , Osborne J. A. "On deriving the electrocardiogram from vectorcardiographic leads." *Clin Cardiol,* 1980, 3(2):87–95.):

$$V1 = -0.515 \times X + 0.157 \times Y - 0.917 \times Z$$

$$V2 = 0.044 \times X + 0.164 \times Y - 1.387 \times Z$$

The two upper drawings are superimposed below to determine the location of the coordinate zero point in the chest. An array of synthesized ECG leads is generated then in parallel-by-parallel mode and a distribution of electric signals along the contour of the heart or chest wall is built. The subsequent three-dimensional reconstruction (as it is currently done using SPECT technology) creates a three-dimensional heart image mapped with normal and pathologic ECG foci.

The myocardium, which is the source of ECG signals, moves with each heart contraction. It has been discovered that an ECG corresponding to a particular visualized (by echocardiography, scintigraphy, fluoroscopy, computed tomography, nuclear magnetic resonance imaging, or other methods) part of the contracting myocardium could be obtained non-invasively by selecting from a plurality of electric signals of the heart those which demonstrate synchronous changes with movements of that visualized part of the myocardium.

Therefore another solution for non-invasively ECG mapping of the heart is to calculate correlation coefficients between displacement of a visualized heart structure and simultaneously synthesized ECGs. The rationale is that as a result of heart movements (contractions) the distance between the sources of cardiac potentials and sensing electrodes changes and of thousands of omnidirectionally synthesized and filtered ECGs the one which exerts a higher correlation coefficient with a selected moving heart structure would be more likely to originate from it. Different statistical techniques are applicable. Curvilinear regression is preferable among the more simple of them.

Figures 10A, 10B:
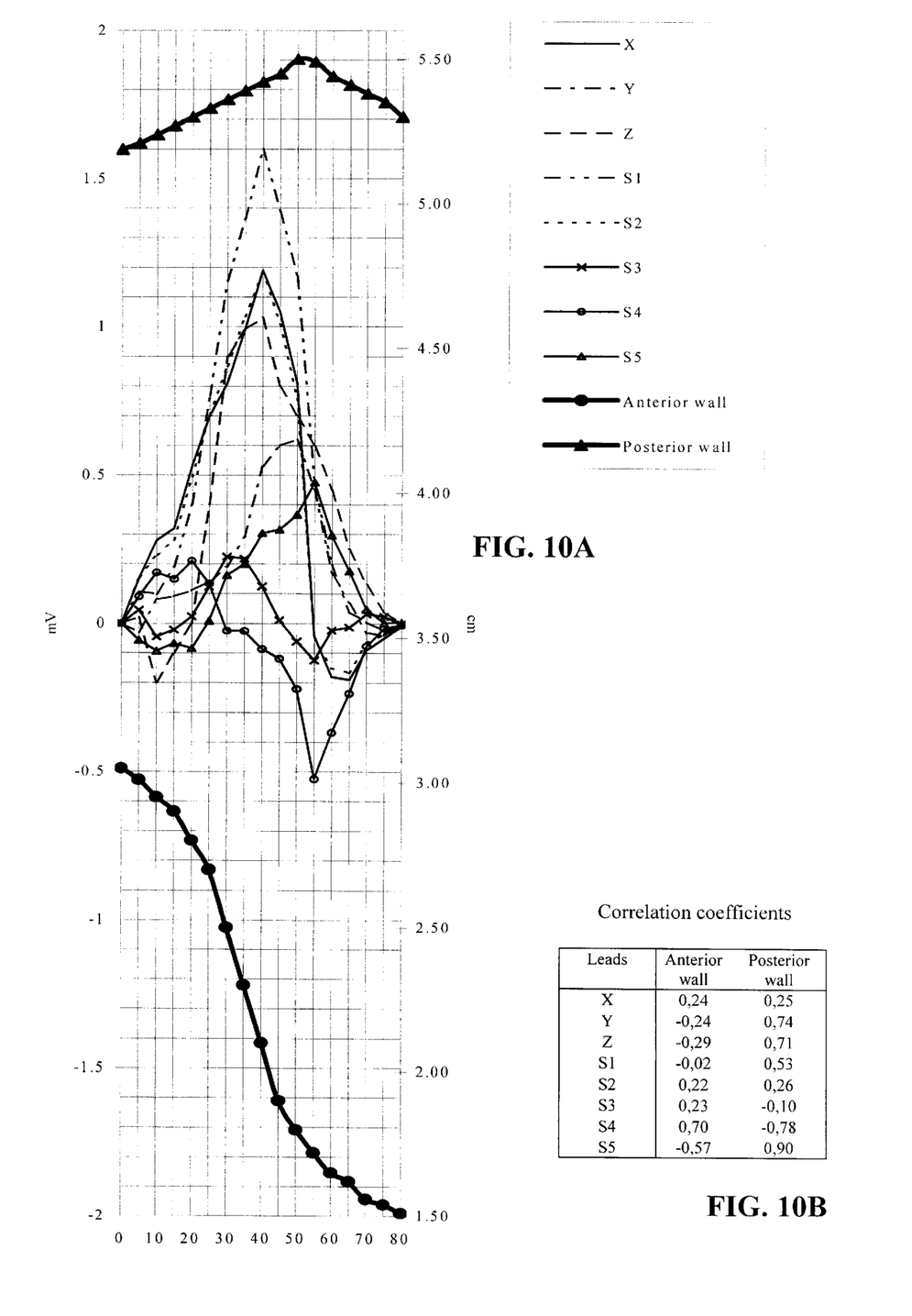
FIG. 10 shows correlation between moving heart structures and synthesized ECGs.

FIG. 10 shows displacement of two points on the anterior and posterior walls of the left ventricle (as seen in M-mode echocardiography) during 80 ms of QRS. The displacement of the anterior wall is most closely related to the tracing in the synthesized lead S4 (correlation coefficient 0.70) while the displacement of the posterior wall better correlates with ECG in lead S5 (correlation coefficient 0.90). Hence it is likely that of eight leads (three orthogonal and five synthesized), lead S4 better reflects the electric activity of the anterior wall while lead S5 does the same for the posterior wall. Ultimately it is possible to non-invasively measure and visualize the electric activity at any point within the heart. Such an imaging technique is particularly valuable when diagnostic accuracy is crucial.

A means for visualizing also displays settings of controllable parameters of signal preprocessing, combining original leads (e.g., scanning pattern, step, sector, time, period, rate), analyzing electric signals (e.g., selection criteria), and adjusting shares of original leads (described below).

A means for controlling parameters of visualizing is used for selecting objects for visualizing pertinent to ECG scanning or the patient, and for adjusting characteristics of a display.

The information indicated above for visualizing can be recorded by an appropriate means onto a suitable carrier (magnetic tape, computer disks, memory cards, paper, etc.) for an off-line analysis, data interchange, storage, documentation, and other purposes.

An ECG scanner includes a means for adjusting for a particular patient shares of original ECG leads in synthesized ECG leads (FIG. 4) so that minimum dissimilarity between original and synthesized leads that are homologous is achieved. The objective of such adjusting is to obtain constants for calculating shares of original leads in synthesized leads that most closely represent electrophysiological characteristics of particular patient, and make ECG scanning more accurate, reproducible, and predictable.

Electrodes placed on a patient do not sense potential differences of the original sources (membranes of cardiomyocytes). Rather, they sense the result of summation, interference, and fading of and adding noise to original potential differences. Therefore original ECG leads used in ECG scanning actually provide with signals that are synthesized from potential differences that could be sensed on cardiomyocytes. Consequently, no practical combination of leads sensed on a patient can reproduce with absolute precision another lead unless the leads sensed on a patient are millions of leads sensing the original potentials of cardiomyocytes. However utilizing conventional leads sensed on a patient to synthesize with acceptable accuracy leads having different spatial positions is achievable and helpful in diagnostics.

Figure 11:
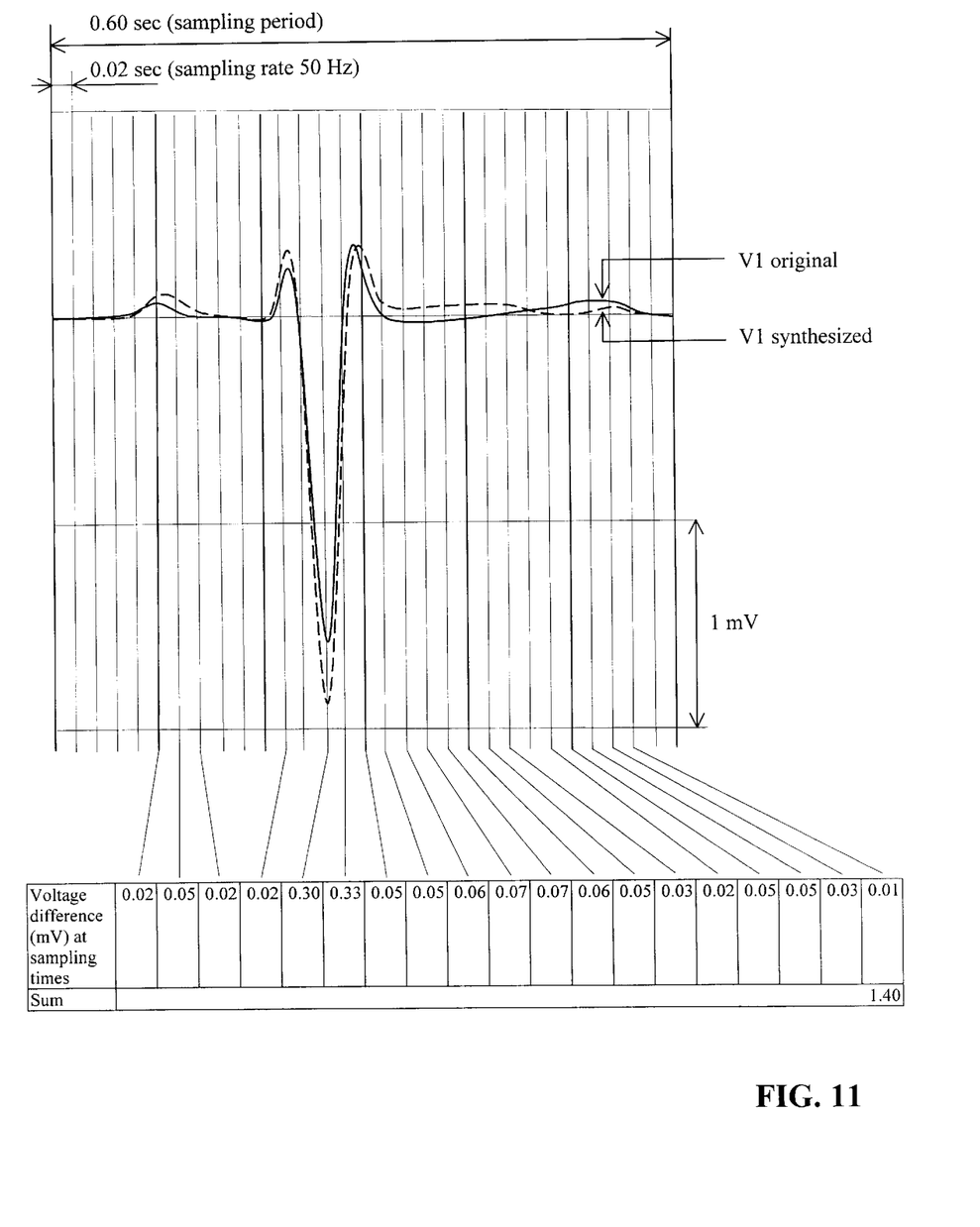
FIG. 11 shows synchronous tracings in original and synthesized homologous leads.

In ECG scanning, leads having any arbitrary positions can be synthesized, including leads that are homologous (i.e. have the same name and spatial position or direction as) to original leads sensed on a patient. Transformation coefficients for synthesizing homologous standard leads from the orthogonal leads are published: 1) Dower G. E. "A lead synthesizer for the Frank system to simulate the standard 12-lead electrocardiogram". *J Electrocardiol,* 1968; 1(1):101–16.2) Dower G. E. , Machado H. B. , Osborne J. A. "On deriving the electrocardiogram from vectorcardiographic leads." *Clin Cardiol,* 1980, 3(2):87–95. For the above reasons, original and synthesized homologous ECGs are similar, but not identical. For example, the ECG in the synthesized lead V1 is similar, but not identical to the ECG in the original lead V1 (FIG. 11). The extent of dissimilarity between homologous original and synthesized leads reflects (among other factors) the match between parameters of combining original leads and electrophysiologic characteristics of a particular patient (individual patterns of origination of electric signals of the heart and their propagation through body tissues). Therefore a quantified dissimilarity between homologous original and synthesized leads is chosen in this invention to measure efficacy of automatically adjusting parameters of combining original leads in a particular patient.

In a preferred embodiment, shares of original leads in synthesized leads are equal to the products of the respective (i) adjusted shares of original leads in three orthogonal leads and (ii) shares of the orthogonal leads in synthesized leads. Furthermore, original leads are the eight active channels of the standard 12-lead electrocardiography.

A means for adjusting computes the adjusted shares by changing the conventional (published) shares of the eight channels in the orthogonal leads in reiterations until a minimum difference between measurements of synchronous electric signals of the eight channels and the homologous eight synthesized leads is achieved. Conventional shares of the eight channels in the three orthogonal leads may be the constants listed in TAB. 1. Reiterations start from a lead yielding the greatest dissimilarity, and the share of the corresponding original lead in the orthogonal leads is increased by a certain amount. The total of voltage differences in the eight pairs of homologues is calculated. If as a result of a reiteration the total decreases, the next reiteration works to reduce the next largest dissimilarity between an original lead and its synthesized homologue. If the total does no longer decrease, reiterations stop, and the resultant adjusted shares are subsequently used for ECG scanning in that patient. If the total increases, the means for adjusting returns to the shares obtained in the previous reiteration, which are subsequently used for ECG scanning in that patient. If the biggest dissimilarity equally shows itself in two or more leads, an adjusting reiteration is performed for each of them, and a set of shares producing better results (the lower total of voltage differences for the eight channels) is selected.

In the subsequent ECG scanning in that patient thus computed adjusted shares of the eight channels in the three orthogonal leads are kept constant while shares of the orthogonal leads (or dihedral angles α and β) serve as independent variables determining positions of synthesized ECG leads.

FIG. 11 illustrates measuring similarity between original and synthesized homologous leads V1. Absolute differences in thirty pairs of voltage measurements made at a sampling rate of 50 Hz over a sampling period of 0.6 sec are listed in the upper row of the table. The differences are summed up in the lower row of the table (1.4 mV). The same procedure is implemented for the rest seven pairs of homologues. The sums of voltage differences in the eight pairs are then aggregated into a total that measures suitability for a particular patient of the selected parameters of combining original leads.

TAB. 5 represents the first reiterations to improve similarity between the original eight channels and eight homologous synthesized ECG leads:

TABLE 5

| Reiteration<br>Increase by 5% of<br>the contribution of: | None | 1<br><br>V1 | 2<br><br>V1 | 3.1<br><br>I | 3.2<br><br>V2 |
|---|---|---|---|---|---|
| I | 1.0 | 1.0 | 1.1 | 1.0 | 1.0 |
| II | 0.8 | 0.9 | 0.9 | 1.0 | 0.9 |
| V1 | 1.4 | 1.2 | 1.0 | 1.1 | 1.0 |
| V3 | 0.0 | 0.1 | 0.2 | 0.2 | 0.2 |
| V4 | 0.3 | 0.3 | 0.3 | 0.2 | 0.3 |
| V5 | 0.5 | 0.4 | 0.4 | 0.3 | 0.4 |
| V6 | 0.3 | 0.3 | 0.2 | 0.3 | 0.2 |
| Total | 5.5 | 5.3 | 5.2 | 5.2 | 5.0 |

The sums of voltage differences in the eight pairs of homologues are entered into column 1 (as noted above, for the V1 homologues it is 1.4 mV). Their total is 5.5 mV. Adjustments are made in reiterations in order to minimize the total. The homologues V1 are most dissimilar. In reiteration 1 the share of lead V1 original in the orthogonal leads is increased by 5%, which results in the total of 5.3 mV (col. 2). The biggest difference then is again lead V1 (1.2 mV). When in reiteration 2 the share of V1 is increased by 5%, the total lowers to 5.2 mV (col. 3). The leads yielding the maximum differences (1.1 mV) are now I and V2. However, an increase in the contribution of lead I into the orthogonal leads does not change the total (reiteration 3.1, col. 4), while an increase in the contribution of lead V2 lowers the total to 5.0 mV (reiteration 3.2, col. 5). Reiteration 3.2 produces more similarity, and its resultants are selected for further adjustment. The leads demonstrating the biggest differences (1.0 mV) are now I, V1, and V2. In the subsequent three reiterations the shares of I, V1, and V2 will be separately increased, the totals they produce will be compared, and the reiteration producing the lowest total will be selected. Then another original lead yielding maximum dissimilarity with its synthesized homologue will be identified and its share increased, and so on until an incremental increase in the share of any of the eight original leads in the orthogonal leads no longer results in better similarity between the eight original leads and their synthesized homologues.

A means for controlling parameters of adjusting regulates the size of an adjusting increase in the share of a lead that produces the greatest dissimilarity, the order for adjusting leads, and a reasonable target for adjustment. For example, if the total of voltage differences for the eight channels of 5 mV had been set as the target value for adjustment, reiteration 3.2 would have been the last in the above example.

The disclosed procedure of adjusting similarity between original and synthesized homologous leads can be used for a set of at least two pairs of homologous leads. Leads composing the set might employ body surface, intracardiac, esophageal, or other electrodes. The more spatially representative is a set of original leads, the more accurate is ECG scanning. New leads with known spatial positions could be added to a set, and their shares adequately adjusted.

It should be understood that instead of the difference in voltage measurements between homologous leads other measures (e.g., a non-coinciding area of homologous ECGs) and algorithms could be utilized in ECG scanning for improving suitability of parameters of combining original leads into synthesized leads in a particular patient.

In manually scanning of the prior art ECG leads are synthesized one by one. Shares of the three orthogonal leads that an investigator selects by adjusting the three potentiometers determine the position of a synthesized lead. Though manually scanning can be accomplished without visualizing the position of a synthesized lead, it becomes easier and more convenient if the position of a synthesized lead is displayed together with a synthesized ECG. In automatically scanning shares of original leads being combined into a synthesized lead are calculated automatically and are unknown to an investigator. Without knowing the position of a synthesized lead interpreting an ECG in it would be impossible and ECG scanning would be worthless.

In order to make positions of synthesized leads known to an investigator, an ECG scanner includes a means for computing positions of synthesized leads (FIG. 4). A position of a synthesized lead can be computed as its coordinates (Cartesian or angular), direction, or image.

Global coordinates of a synthesized ECG lead are generally difficult to comprehend (unless an investigator is a cardiologist also experienced in navigation). Building an image of a synthesized lead on a display considerably facilitates understanding its three-dimensional position. A lead may be displayed, for instance, as a lighting vector inside a transparent model of a human torso, or as an arrow on a three-dimensional screen. In a preferred embodiment, a three-dimensional image of a synthesized lead is computed as an arrow on the background of a graduated globe imitating the space available for ECG scanning and having landmarks of the 12 standard leads and three orthogonal leads.

Shares of orthogonal leads in a synthesized lead are particularly instrumental for computing an image of a synthesized lead, because the coordinates of an image could be expressed by the respective shares of the three orthogonal leads. In a preferred embodiment, a means for computing positions of synthesized leads computes shares of orthogonal leads in a synthesized lead based on independent variables determining the direction of a synthesized lead (such as a pair of dihedral angles $\alpha$ and $\beta$). For displaying a three-dimensional image of a synthesized lead on a regular two-dimensional monitor, shares of orthogonal leads may be transformed into a three-dimensional simulation format.

An ECG scanner could be designed as a separate diagnostic instrument or as a part of an electrocardiograph, ECG monitor, or a system for ECG stress testing to improve their diagnostic capabilities. Without ECG scanning much useful information that could be derived from the conventional 12-lead ECG or VCG is lost. ECG scanning has considerable advantages over and can enhance or substitute for the conventional 12-lead ECG, VCG, and BSPM, and effectively supplement any cardiac investigation. ECG scanning is easy to use, does not require much extra training for physicians, and is relatively inexpensive. It is promising in ischemia, infarction, ventricular preexcitation, arrhythmia, conduction blocks, and other disorders. Matching morphological and electrophysiological changes in the heart with the help of ECG scanning is of a particular diagnostic interest.

Although only a limited number of specific embodiments have been described in detail, such description is not to be taken as a limitation of the present invention. The description has been given only as illustration and example. To those skilled in the art, it will be readily apparent that changes may be made without departing from the spirit of the disclosed inventive concepts. The scope of the invention is to be defined by the appended claims.

I claim:

1. An electrocardiographic scanner for automatically scanning a three-dimensional space formed by a plurality of synthesized electrocardiographic leads, said scanner having original electrocardiographic leads that have known positions in the space and said scanning accomplished by systematically combining the original leads into an array of the synthesized leads that have arbitrary positions in the space, said scanner including:

a means for calculating in a predetermined order shares of the original leads in the non-orthogonal equally spaced synthesized leads wherein said shares reflect spatial interrelations between the original leads and the synthesized leads, and a means for acquiring synchronous electric signals of the original leads and combining the signals in accordance with said shares.

2. The scanner of claim 1 wherein both said means are adapted for the original leads of eight active channels of the standard 12-lead electrocardiography.

3. The scanner of claim 1 wherein both said means are adapted for the original leads of body surface potential mapping.

4. The scanner of claim 1 wherein both said means are adapted for the original leads of vectorcardiography.

5. The scanner of claim 1 wherein said means for calculating calculates said shares as equal to the products of the respective (i) shares of the original leads in three orthogonal leads and (ii) shares of the orthogonal leads in the synthesized leads.

6. The scanner of claim 1 including a means for controlling parameters of either or both of said means.

7. The scanner of claim 1 including a means for measuring the signals combined thereby and for selecting measurements meeting predetermined criteria.

8. The scanner of claim 7 wherein said criteria include extremeness of said measurements.

9. The scanner of claim 7 wherein said criteria include being in a predetermined relationship with predetermined values.

10. The scanner of claim 1 including a means for visualizing the signals combined thereby.

11. The scanner of claim 10 wherein said means for visualizing is a means for continuous electrocardiographic monitoring.

12. An electrocardiographic scanner for automatically scanning a three-dimensional space formed by a plurality of synthesized electrocardiographic leads, said scanner having original electrocardiographic leads that have known position in the space and said scanning accomplished by systematically combining the original leads into an array of the synthesized leads that have arbitrary positions in the space, said scanner including:

a means for calculating in a predetermined order shares of the original leads in the synthesized leads wherein said shares reflect spatial interrelations between the original leads and the synthesized leads, a means for acquiring synchronous electric signals of the original leads and combining the signals in accordance with said shares, and a means for matching the signals combined hereby with heart structures of a patient for whom said scanning is performed.

13. An electrocardiographic scanner for automatically scanning a three-dimensional space formed by a plurality of synthesized electrocardiographic leads, said scanner having original electrocardiographic leads that have known positions in the space and said scanning accomplished by systematically combining the original leads into an array of the synthesized leads that have arbitrary positions in the space, said scanner including:

a means for calculating in a predetermined order shares of the original leads in the synthesized leads wherein said shares reflect spatial interrelations between the original leads and the synthesized leads, a means for acquiring synchronous electric signals of the original leads and combining the signals in accordance with said shares, and a means for adjusting for a particular patient said shares to have minimum dissimilarity between the original leads and the synthesized leads, which are homologous to these original leads.

14. The scanner of claim 13 wherein the shares of the original leads in the synthesized leads are equal to the products of the respective (i) shares of the original leads in three orthogonal leads and (ii) shares of the orthogonal leads in the synthesized leads, and wherein said means for adjusting adjusts the known shares of the original leads in the orthogonal leads.

* * * * *